(12) United States Patent
Fischer

(10) Patent No.: US 8,303,626 B2
(45) Date of Patent: Nov. 6, 2012

(54) DEVICE FOR THE DECOMPRESSION AND THERAPY OF THE CERVICAL SPINAL COLUMN

(75) Inventor: Paul Walter Fischer, Fronters du Razes (FR)

(73) Assignee: CuraCeres GmbH, Sachseln (CH)

( * ) Notice: Subject to any disclaimer, the term of this patent is extended or adjusted under 35 U.S.C. 154(b) by 484 days.

(21) Appl. No.: 12/529,510

(22) PCT Filed: Feb. 29, 2008

(86) PCT No.: PCT/EP2008/052504
§ 371 (c)(1),
(2), (4) Date: Sep. 1, 2009

(87) PCT Pub. No.: WO2008/107392
PCT Pub. Date: Sep. 12, 2008

(65) Prior Publication Data
US 2010/0094342 A1    Apr. 15, 2010

(30) Foreign Application Priority Data
Mar. 2, 2007 (CH) .................................. 0348/07

(51) Int. Cl.
*A61F 5/00* (2006.01)
(52) U.S. Cl. ............... 606/241; 602/13; 602/18; 602/32

(58) Field of Classification Search .............. 601/23, 601/39, 148, 149, 150; 602/5, 12, 13, 17, 602/18, 19, 32, 33, 35, 36; 606/204, 237, 606/240, 241; 128/845, 846, DIG. 20, DIG. 23; 5/637, 344, 915, 932
See application file for complete search history.

(56) References Cited

U.S. PATENT DOCUMENTS

| 5,454,781 | A | * | 10/1995 | Chitwood | 602/18 |
| 5,662,597 | A | * | 9/1997 | Chitwood | 602/32 |
| 5,709,649 | A | * | 1/1998 | Chitwood | 602/32 |
| 5,713,841 | A | * | 2/1998 | Graham | 602/32 |
| 5,752,927 | A | * | 5/1998 | Rogachevsky | 602/18 |
| 6,447,468 | B1 | * | 9/2002 | Hankins et al. | 602/18 |
| 7,670,307 | B2 | * | 3/2010 | Chitwood et al. | 602/13 |

* cited by examiner

Primary Examiner — Quang D Thanh
(74) Attorney, Agent, or Firm — CUSPA Technology Law Associates; Yi Li

(57) ABSTRACT

The present invention relates to a device comprising a shaped shoulder piece to rest on the shoulders of a person to be treated, and a shaped head piece to be laid on it, as support for the chin and two bottom points of the rear lower edge of the skull. This ensures a three-point support of the head on the top side of this shaped head piece. Further, the device comprises a lifting mechanism, which is inserted between the back of the shaped shoulder piece and the shaped head piece. This lifting mechanism is simply a pump in the form of a bellows with a one-way valve for discharge, by which the air cushion can be inflated and discharged arbitrarily.

7 Claims, 5 Drawing Sheets

DEVICE FOR THE DECOMPRESSION AND THERAPY OF THE CERVICAL SPINAL COLUMN

CROSS REFERENCES TO RELATED APPLICATIONS

This application is a national phase of PCT patent application No. PCT/EP2008/052504, filed Feb. 29, 2008, which claims priority of Switzerland Patent Application No. 00348/07, filed Mar.2, 2007.

BACKGROUND OF THE INVENTION

The present invention relates to a device to relieve the spine in the cervical area and treat it regularly. Many people suffer from headaches, which are often caused by the spine, especially by the neck area of the spine, that is from the cervical area. Further, there are many people who have suffered a whiplash injury and are suffering chronic pain in the neck area. The spine in the neck area must constantly bear the weight of the head and receive and absorb all moments caused by head movements. Accordingly, it is loaded and if damaged due to accidents or wear, it is very sensitive.

So far, a device is lacking by which a relief of such pain caused by the neck and spine and any discomfort of suffering humans could be easily achieved at home or even on trips and which device would be easy to operate, specifically adjustable and to be used individually for treatment. Physiotherapists confirm that a load relieving, and especially a periodic load relieving and loading of the cervical spine is good for the wellness and very beneficial for a healing process. This fact has been confirmed and corroborated by practical experience.

It is therfore the object of the present invention to provide a device for relieving and treating the cervical spine, which is easy to use, either at home or on a trip, and which allows a focussed, individually-controlled load relieving of the spine in neck area. The device will also allow for a targeted treatement, namely a periodic relieving and loading of the spine in the cervical aera.

BRIEF SUMMARY OF THE INVENTION

The problem is solved by a device for load relieving and treating the cervical spine, consisting of a shoulder rest and a therefrom liftable head support the neck and chin, and a lifting means between the back of the shoulder rest and head support.

This device and its components and its construction will be described with reference to the following drawings in detail, and its function will be commented and explained.

BRIEF DESCRIPTION OF THE SEVERAL VIEWS OF THE DRAWINGS

It shows.

DETAILED DESCRIPTION OF THE INVENTION

Figure 1:
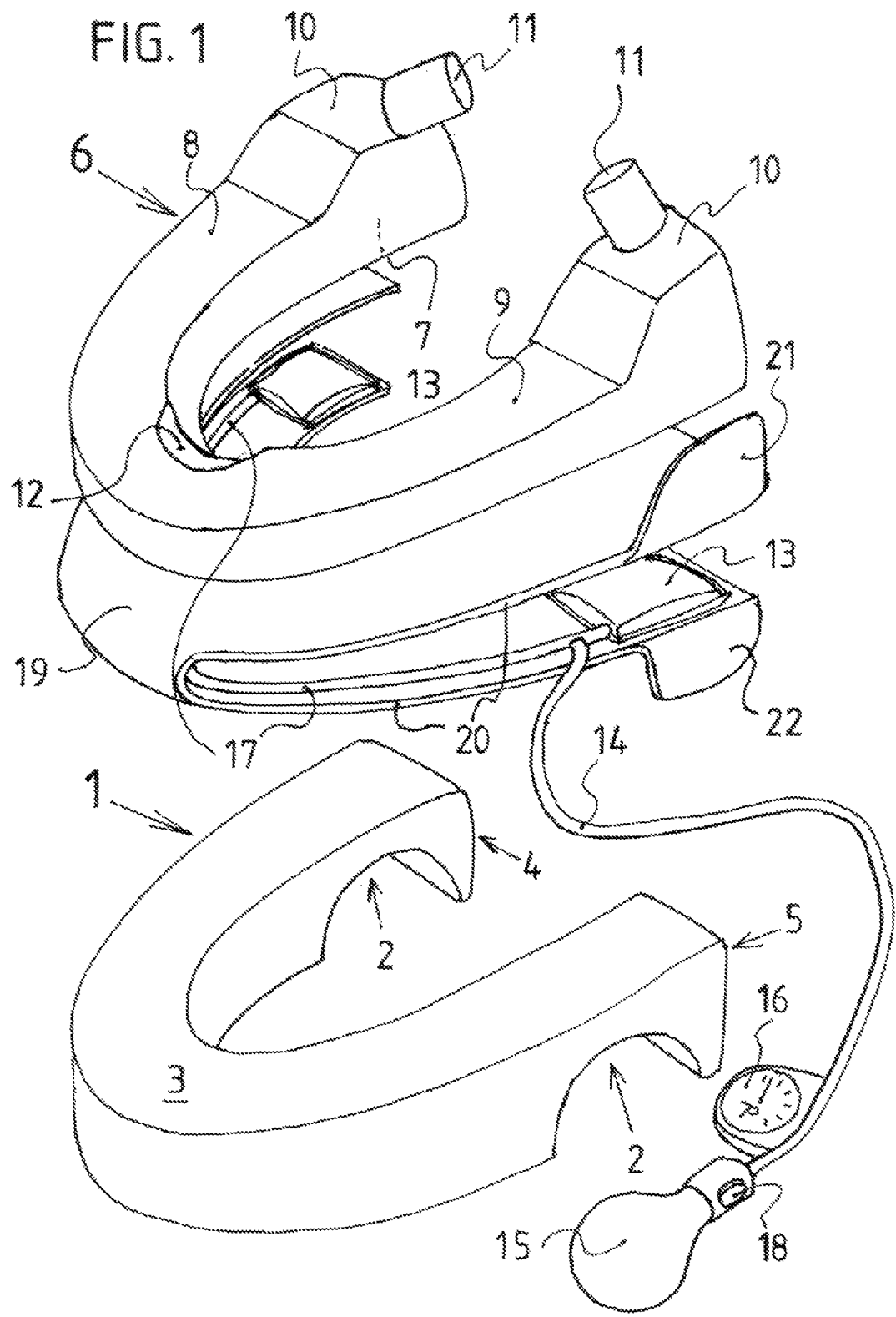
FIG. 1: The various components of the device, separately arranged and represented above each other.

FIG. 1 shows all the components of the device. This device consists of a shaped shoulder piece 1 made of a lightweight, elastic material such as polystyrene or similar. Polystyrene is indeed an amorphous, partly crystalline thermoplastic. This material is known under trade names such as Lustron, Styrofoam, Styrodur, Styroflex, Sagex (in Switzerland) and Telgopor (in the Spanish speaking world). This shaped shoulder piece 1, however, can also be manufactured from an alternative material with similar characteristics. It can have a wood or a plywood body, or consist of foamed plastic material or a blown hollow plastic body. Advantageously, the shaped shoulder piece is surrounded by a textile material which is replaceable, and therefore can be designed as a shaped pocket with one or more zippers, or with Velcro or snaps in order to close that pocket. In another variant of the shaped shoulder piece it may also be coated with a suitable material that feels comfortable on the skin, and is also easy to wash. This shaped shoulder piece has the shape of a horseshoe or is shaped as a U with its two branches 4,5 and whose lower rear side there is a channel-like recess 2 which does extend perpendicularly to the horseshoe-shaped or U-shaped piece. With this recess 2, the shaped piece 1 is determined to rest on the shoulder of a person to be treated. The top surface 3 of the shoulder shaped piece 1 is even. In order to apply it, the two branches 4,5 of the horseshoe-shaped piece are being spread apart slightly and elasticly, so that the shaped shoulder piece 1 can be shifted onto to shoulders from the front side, enclosing the neck of the person to be treated, so that the channel-like recesses 2 rest on the two shoulders of the person. When the shaped piece is too stiff, it can be designed with a hinge with vertical pivot axis at its front so the two branches extending to the rearside can swivel away from each other. This shaped shoulder piece 1 is made a few inches thick so that despite its recess 2 on its lower side it nevertheless forms a flat upper surface. The clear width between the two branches 4 and 5 is such that they can enclose necks of all collar sinzes.

The second essential component of the device is the shpaed head piece 6, which can also be enclosed by a fabric bag or can be lined with a textile fabric or may be coated. This piece 6 is made from the same material as the shaped shoulder piece 1 and also forms a horseshoe-shape or a U. The lower side 7 of the shaped head piece 6 is even while on the top side, toward the end side of the branches, there is an increase 10 on each branch, and on the inner upper side of said increase there is a bump 11 extending oblique to the top. In the front of the top side of the circular section of the shaped head piece 6 there is a recess 12 which fits to the chin of a person to be treated. The bumps 11 also provide support points, namely for the bottom end of the skull, left and right of the cervical spine, thus allowing a three-point support of the head or skull with its chin on top of the shaped head piece 6. In a variant, these bumps 11 can be made as separate cylindrical parts, manufactured of rubber, plastic, wood or polystyrene, and they are then inserted into corresponding holes on the two branches of the shaped piece 6. Thereby, bumps 11 of different hights can be inserted, depending on the anatomical conditions of the person to be treated. The top or support surface of these bumps 11 may be better suited to the requirement on the skull by tailoring, so that a convenient fitting will be attained. This shaped head piece 6 may also be constructed in such way that it consists in essence of a U-shaped metal profile, which is equipped with a form piece pad on the front as a chin rest. This chin rest can be attached to the profile by screws in a hight-adjustable manner, so that the chin rest is individually adjustable. At both ends of the branches of the U-shaped metal profile there are adjustable support bumps provided which are adjustable via screws in their place, in their angles of incidence and their hight. In the front area of the metal profile a hinge may be arranged so that the two branches are adjustable in their pivotal position. The length of the two laterally extending sections or branches is also adjustable, for example by consting two parts which are overlapping each other or which are telescopically guided on each other and which are fixable in each state of extension. Thus, the length of the shaped head piece 6 can be adjusted individually and precisely to any person, either as a whole as well as in respect to the position and height of the chin rest and the two humps.

As another indispensable element, a lifting means pertains to this device which acts between the two superimposed form pieces 1,6 and by which the shaped head piece 6 can be lifted from the lower shaped shoulder piece 1. The most simple and best suited means is a pneumatically-acting lifting device. In the shown example, it consists of two air cushions 13, which are layed in between the two rear sides of the device, that is between the branches 8,9 of the upper 6 and lower shaped piece 1. These two air cushions 13 are connected via a hose 17 with each other and are inflatable via a hose 14 on whose end a rubber bellows 15 is mounted. The hose 14 is also equipped with a relief one-way-valve 18 with a spring-loaded push-button to open the valve 18. In addition, a manometer 16 can be built into the hose 14, for displaying the air pressure prevailing in the cushion 13.

In the example shown, the device even includes a V-shaped intermediate plate 19 made of plastic, metal or plywood. This includes a sharp angle when seen from the side, and its outer edges 20 extend along the outer contour of the other two pieces, namely the shoulder- 1 and the head piece 6. This intermediate plate 19 has on each of its upper branches on their rear and outer side an upwardly protruding ear 21, and if need be also on the lower branches of the plate a downward projecting ear 22 so that the shaped head piece 6 is held between these two ears 21 or at least guided, and the shaped shoulder piece 1 in like manner between the downwards protruding ears 22. This device is now applied in such way that initially, the shaped shoulder piece 1 is shifted from the front onto the shoulders of a person to be treated. Of course this person can put on this shaped shoulder piece as well as the entire device by himself without any problems. Once the shaped shoulder part 1 is being placed, as next the shaped head piece 6 is being shifted from the front onto the flat top of the shoulder-shaped piece 1. To facilitate this, the two branches 8,9 must be sligthly spread apart from each other and they are afterwards closed elastically by releasing them again. Now, the person's chin rests on the recess 12 on the shaped head piece 6, and the two bumps 11 at the rear top of the branches 8,9 support the bottom of the skull on its back side. This provides a proper three-point support. Next, the intermediate plate 19 which shows a similar horseshoe-shape when seen from above, is inserted from the front between the shaped shoulder piece 1 and shaped head piece 6. For this it is initially being compressed, which means the two branches of the V-shape are being closed entirely or almost. Then they the intermediate plate 19 can be easily inserted between the pieces 1,6. It will then relax and spread back elastically into the initial form shown here, in which the two pieces 1,6 are slightly being spread apart on their rear side and are spaced from each other. Now the two air cushions 13 can be inserted between the two branches of the intermediate plate 19, so that they are placed left and right between the two branches 4,8 and 5,9 of the two shaped pieces 1,6. In this initial position, the head of the person to be treated is stabilized, but not yet relieved from the shoulder. The cushion 13 can now be inflated by the person to be treated by squeezing the bellows 15.

This should be carried out consciously by the person himself, since he can, by pumping, smoothly dose the tension on his cervical spine to cause a comfortable to a just bearable tension in his cervical spine. Conversely, he can immediately reduce and eliminate the tension on demand or when an acute pain should occur, by operating the relief valve 18, for which he only needs to press the corresponding spring-loaded push button. This device shown here can also be used without the intermediate plate 19. In this case, the air cushions 13 are directly inserted between the rear areas of the branches 4,8 and 5,9 of the two pieces 1,6.

Figure 2:
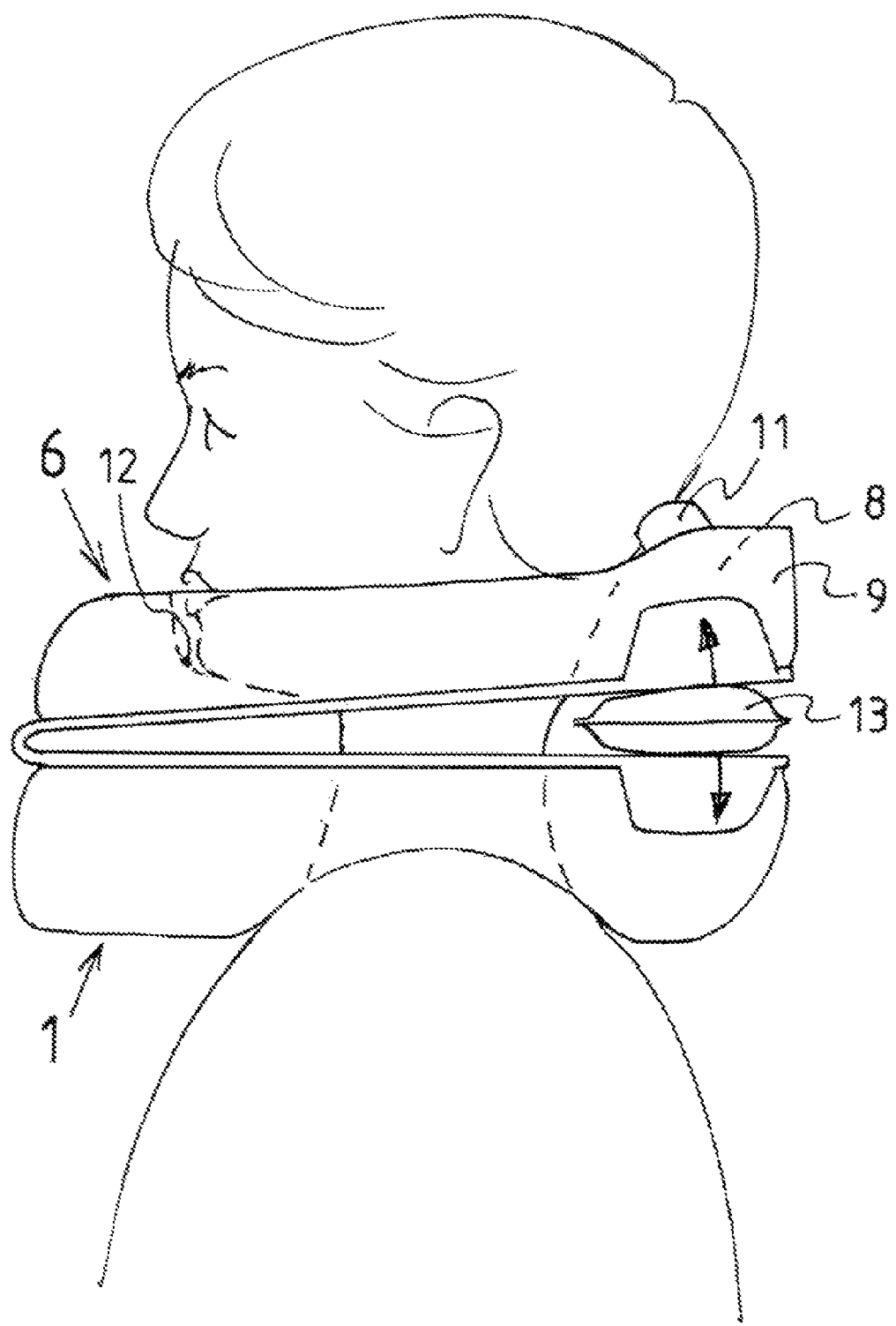
FIG. 2: The device applied to treat a person, seen from the side.

In FIG. 2, the device is shown when applied to a person to be treated, viewed from the side. The lower shaped shoulder piece 1 is resting on the shoulder, while the upper shaped piece 6, namely the shaped head piece 6, supports the person's head on three points, namely on the chin by the recess 12, and at the lower edge of the skull by the bumps 11 on the upper side of the branches 8,9 of the shaped head piece 6. Between these two pieces 1,6 the air cushions 13 are placed. It can also be a single air cushion 13 which extends across the width of the device, that is extending transversely behind the neck of the person between the two branches of the two pieces 1,6. The air cushions 13 can be secured, e.g. on the shaped piece 1, using Velcro strips mounted on them against a slip on the bottom of the shaped piece 1. If the bellows 15 is operated by using the associated pumping device, the two pieces 1,6 with their rear ends are being spread apart as shown by the arrows, while they lay on each other in the front. Depending on the measure of spreading, the spine of the treated person is more or less relieved in the neck area.

Figure 3:
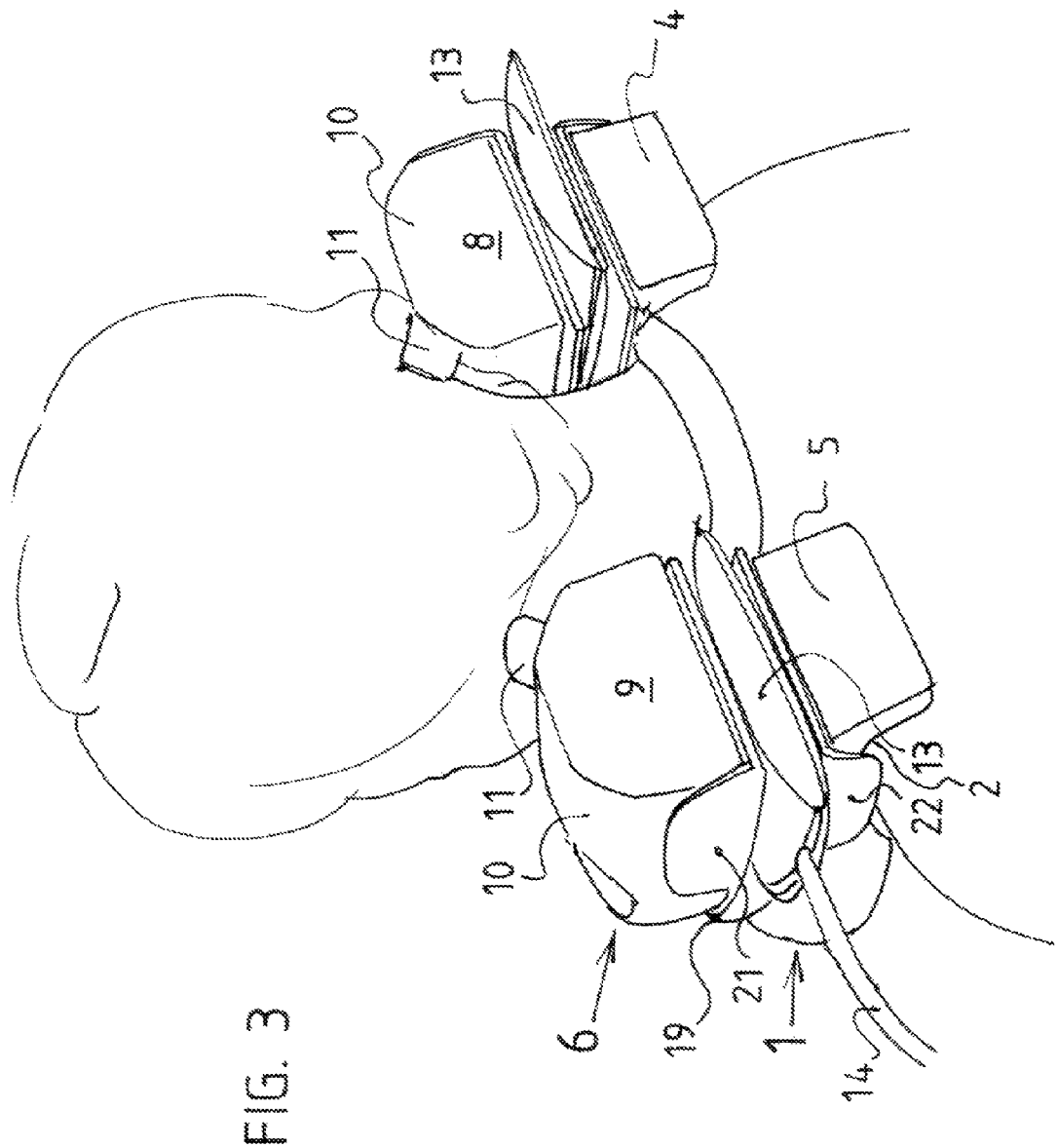
FIG. 3: The device applied to treat a person, viewed obliquely from behind.

FIG. 3 shows the device applied to a person to be treated, viewed obliquely from behind. It can be seen that the two pieces 1,6 are open on their back side, since the two branches 4,5 end there. Due to the nature of the material of pieces 1,6, their legs can be slightly spread apart what faciliates the putting on of initially the shaped shoulder piece 1 and thereafter the shaped head piece 6. The recess 2 for the shoulder of the person ensures a good fitting of the shaped shoulder piece 1 and for the shaped head piece 6, the three-point support is important.

Figure 4:
FIG. 4: The device applied to treat a person, viewed obliquely from the front.

In FIG. 4, the device is applied to a person to be treated, seen obliquely from the front. The curvature on the inner side of the shaped head piece 6 provides plenty of space for the cheeks and the neck. For not quite slim people, e.g. such ones having a double chin or being stocky build with only a short neck, this space is particularly needed. Particularly useful and beneficial to the well-being is a periodic relieve back and again streching of the cervical spine what is confirmed by many physiotherapists. This therapy can be performed with the device presented here extremely effective and extremely easy and conveniently, and this by the person to be treated itself.

Figure 5:
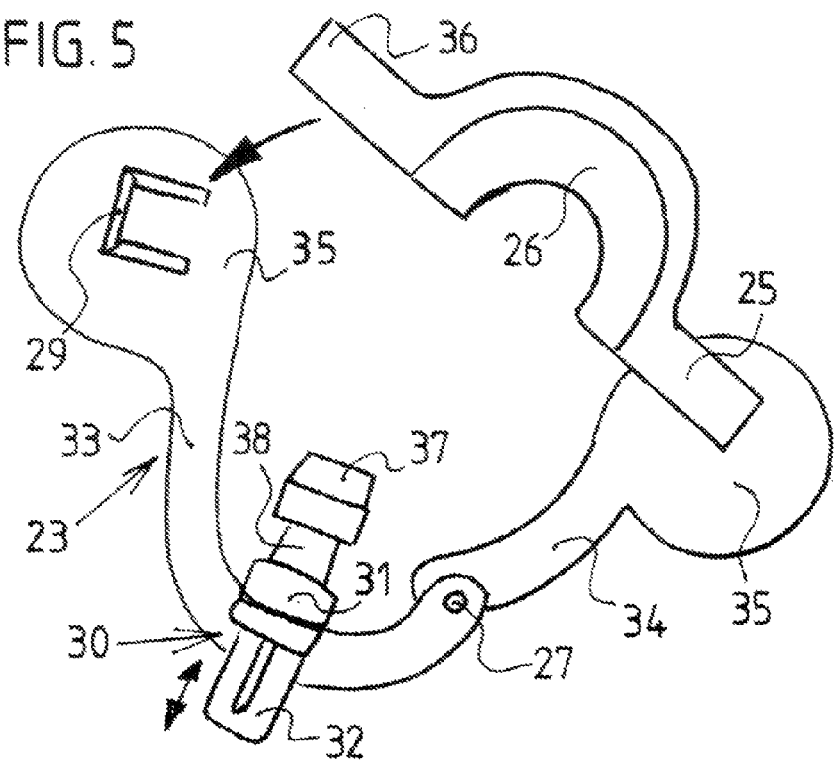
FIG. 5: An alternative method with open branches, seen from above.

FIG. 5 shows an alternative embodiment of the device. It consists of a head-side form plate 23, which forms two branches 33,34, a longer branch 33 and a shorter branch 34 which are pivotally connected to each other by a hinge 27. At their ends, these branches 33,34 are formed into a circular support plate 35 each. This entire form plate 23 can be made of a plastic plate, or from a strong foam, which can be coated so that it can be washed off and thus is easy to clean. On the one circular support plate 35, here that one at the end of the branch 34, there is an interlock 25 attached with its local end.

It extends to the opposite branch 33 and its middle part forms an arc so that its inner side forms a padded funnel-shaped supporting surface to provide a headrest 26. When the two branches 33,34 will be swung around the hinge 27 toward one another, along the shown curved arrow, then the free end 36 of the interlock 25 finally comes to a rest on the circular support plate 35 of the branch 33. On this support plate 35, catching ribs 29 are formed. Once the free end 36 of the interlock 25 is interlocked with these catching ribs 29, a closed and fixed lock is attained with it. The device that forms with its two branches 33,34 is no longer merely a horseshoe shape, but a fixed and closed ring. By these two pivotable branches 33,34, the device is much easier to put on the neck of a person. With open branches 33,34 it is being put on, and afterwards the branches 33,34 are pivoted around the neck of the person and the interlock 25 is finally latched, thereby providing a stable and solid ring around the neck/shoulder area of the person to be treated. The neck support 26 then is fittingly adjusted to the neck of the person. On the opposite, front side of the device there is a chin rest 30 mounted on the branch 33. This chin rest 30 sits on an adjustable plate 32, sliding along the drawn arrows, which carries a protruding upward, soft chin pad 31. The chin rest 30 is adapted to the chin of the person to be treated and then secured in the correct position. Then, the chin pad 31 sits on the chin of the person and supports it. On the lower side of the branch 33, below the chin rest 30, there is a chest pad 37 which is held by a bracket 38, adjustable in length which is attached on the bottom of the branch 33. This bracket 38 can be adjusted to that extent that the end-side chest pad 37 rests on the breastbone of the person to be treated and therefore supports the device against the breast.

Figure 6:
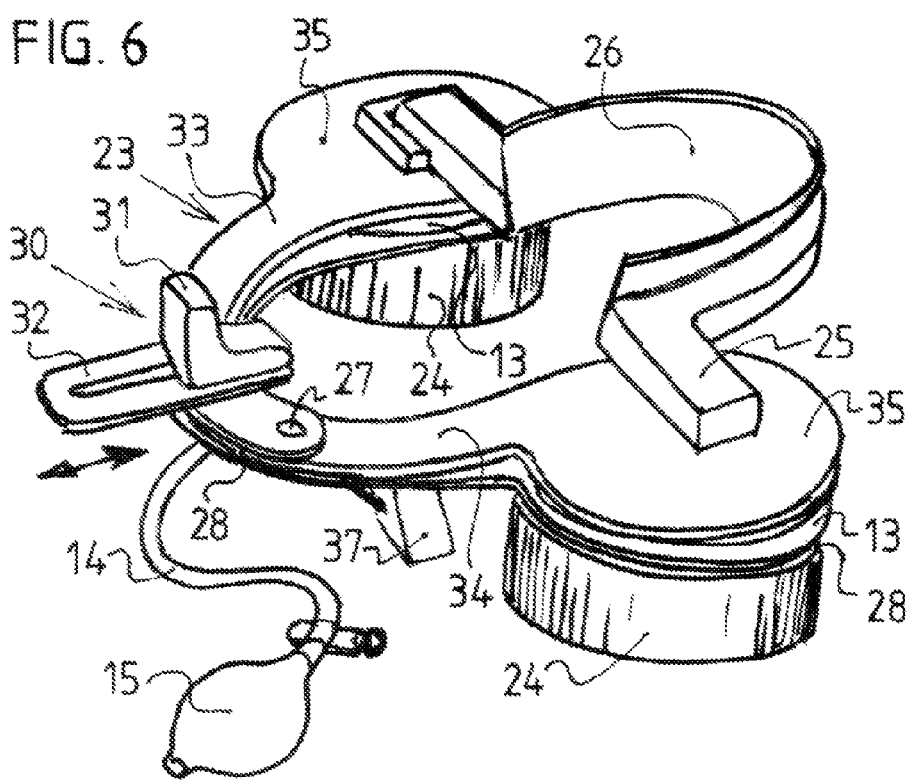
FIG. 6: The alternative device shown in FIG. 5 in closed position, when applied.

FIG. 6 shows the device in use position, with closed branches 33,34. At the bottom of the mold plate 30 there is an elastic plastic plate 28 fastened, but only in the sector of the bent branches 33,34. Toward the end-side support bars 35, the plastic plate 28 is loose and can therefore be easily bent downwards from the supporting plate 35. At the top of this plastic plate and below the support plate 35 there is an air cushion 13 which has the same basic shape as the overlying support plate 35 when void of air. It is supplied with air via a hose 14. This tube 14 is equipped on one side with a rubber bellows 15. By compressing, air is pumped into the air cushion 13 and the plastic plate 28 is spread away from the supporting plate 35. On the lower side of the plastic plate 28, below the support plates 35, cylindrical foam pads 24 are attached, for example, by using Velcro or snaps. These foam pads 24, when the device is used, are located on the shoulders of the person to be treated. They can be replaced by more or less high pads so that for each and any patient the best fitting of the device can be achieved. The device is well placed to a person when their its neck is fittingly supported by the neck support 26, then chin resting on the chin pad 31 and the device is supported by the chest pad 37 on the breastbone. By inflating the cushions, the neck will gently be lifted up on the support on both shoulders.

It is clear that the device and its function can be realized by modified designs. The main thing is that a shoulder pad is present, on which a liftable head rest for the neck and chin area are available, as well as a lifting means 13 between the rear area of the shoulder pad and head support.

The invention claimed is:

1. A device for relieving and treating the cervical spine of a person, comprising a shoulder rest and a head support for neck and chin area, a pneumatic lifting means including a bellows for pumping air via a supply hose to air cushions disposed between a back of the shoulder rest and the head support, and an one-way-valve and a pressure gauge for measuring and displaying an internal pressure in the air cushions, wherein the head support comprises a form plate having two branches that are pivotally connected to each other by a hinge, each branch having a support plate located at one end of the branch, wherein the support plates are force-fittingly connectable with each other, and the shoulder rest comprises two plastic plates, each plastic plate attached on a lower side of the branches, each plastic plate is provided with one of the air cushions on an upper side of the plastic plate, below the support plate, and each plastic plate is provided with a shoulder pad detachably disposed on a lower side of the plastic plate.

2. The device for relieving and treating the cervical spine according to claim 1, wherein the two plastic plates of the shoulder rest are elastically bendable.

3. The device for relieving and treating the cervical spine according to claim 1, wherein the shoulder rest is attached to the lower side of the branches in a manner that toward a back of the support plates the two plastic plates are loose and can be bent downwards from the support plates.

4. The device for relieving and treating the cervical spine according to claim 1, wherein the two branches which are swivel-mounted toward each other are force-fittingly interlockable with each other by an interlock mounted on one of the branches.

5. The device for relieving and treating the cervical spine according to claim 1, wherein the two branches which are swivel-mounted toward each other are force-fittingly interlockable with each other by an interlock mounted on one of the branches, and said interlock forms a neck support when the branches are in their closed state.

6. The device for relieving and treating the cervical spine according to claim 1, wherein an adjustable chin pad is mounted on an upper side of one of the branches, and a chest pad is provided on a lower side of one of the branches, the chest pad is adjustable in height.

7. The device for relieving and treating the cervical spine according to claim 1, wherein the head support forms a support surface for a rear lower edge of a skull when the branches are in their closed state and an interlock is locked, and a chin pad provides a support surface for the chin, for building a stable and definite multi-point-support for the head.

* * * * *